United States Patent [19]

Sunderland

[11] Patent Number: 5,163,916
[45] Date of Patent: Nov. 17, 1992

[54] SAFETY SYRINGE WITH OFFSET NEEDLE
[75] Inventor: Richard A. Sunderland, Creve Coeur, Mo.
[73] Assignee: Sherwood Medical Company, St. Louis, Mo.
[21] Appl. No.: 655,201
[22] Filed: Feb. 11, 1991

Related U.S. Application Data

[63] Continuation of Ser. No. 461,603, Jan. 5, 1990, abandoned.

[51] Int. Cl.⁵ .................................................. A61M 5/32
[52] U.S. Cl. ..................................... 604/198; 604/110; 604/263
[58] Field of Search ................ 604/110, 187, 192–198, 604/239, 240, 263, 272

[56]  References Cited

U.S. PATENT DOCUMENTS

| | | | |
|---|---|---|---|
| 2,571,653 | 10/1951 | Bastien | 128/218 |
| 2,899,959 | 8/1959 | Ginsburg | 604/272 X |
| 3,326,206 | 6/1967 | Barr, Sr. et al. | 604/239 X |
| 3,459,342 | 8/1969 | Manning | 604/192 X |
| 3,520,292 | 7/1970 | Barr, Sr. et al. | 128/2 |
| 3,780,734 | 12/1973 | Wulff | 128/218 R |
| 3,822,701 | 7/1974 | Cloyd | 604/192 |
| 3,890,971 | 6/1975 | Leeson et al. | 128/218 R |
| 4,139,009 | 2/1979 | Alvarez | 128/218 N |
| 4,266,544 | 5/1981 | Wardlaw | 604/110 |
| 4,356,822 | 11/1982 | Winstead-Hall | 128/215 |
| 4,425,120 | 1/1984 | Sampson et al. | 604/198 |
| 4,573,976 | 3/1986 | Sampson et al. | 604/198 |
| 4,604,654 | 5/1987 | Strauss | 604/198 |
| 4,631,057 | 12/1986 | Mitchell | 604/198 |
| 4,643,199 | 2/1987 | Jennings, Jr. et al. | 128/763 |
| 4,650,468 | 3/1987 | Jennings, Jr. | 604/110 |
| 4,655,751 | 4/1987 | Harbaugh | 604/198 |
| 4,659,330 | 4/1987 | Nelson et al. | 604/192 |
| 4,666,435 | 5/1987 | Braginetz | 604/198 |
| 4,681,567 | 7/1987 | Masters et al. | 604/198 |
| 4,693,708 | 9/1987 | Wanderer et al. | 604/198 |
| 4,695,274 | 9/1987 | Fox | 604/198 |
| 4,723,943 | 2/1988 | Spencer | 604/198 |
| 4,731,059 | 3/1988 | Wanderer et al. | 604/192 |
| 4,737,144 | 4/1988 | Choksi | 604/198 |
| 4,743,233 | 5/1988 | Schneider | 604/192 |
| 4,782,841 | 11/1988 | Lopez | 128/164 |
| 4,795,443 | 1/1989 | Permenter et al. | 604/198 |
| 4,801,295 | 1/1989 | Spencer | 604/198 |
| 4,822,343 | 4/1989 | Beiser | 604/187 |
| 4,842,587 | 6/1989 | Poncy | 604/198 |
| 4,844,089 | 7/1989 | Roberti | 128/764 |
| 4,874,383 | 10/1989 | McNaughton | 604/198 |
| 4,911,706 | 3/1990 | Levitt | 604/198 |
| 4,915,696 | 4/1990 | Feimer | 604/192 |
| 4,929,237 | 5/1990 | Medway | 604/198 |
| 4,946,447 | 8/1990 | Hardcaste et al. | 604/198 |
| 5,000,167 | 3/1991 | Sunderland | 128/763 |

OTHER PUBLICATIONS

*The Random House College Dictionary: Unabridged edition,* Jess Stein, ed., (Random House, Inc., 1980, New York, pp. 95, 778).
*Webster's Ninth New Collegiate Dictionary,* (Merriam–Webster, Inc., 1984, pp. 121, 694).

*Primary Examiner*—John D. Yasko
*Assistant Examiner*—Adam J. Cermak
*Attorney, Agent, or Firm*—Andrew J. Beck; Montgomery W. Smith; Richard D. Allison

[57]  ABSTRACT

A medical device particularly adapted for use with a syringe including a nonlinear needle or a nonlinear protective shield wherein the protective shield is movable between a needle exposing retracted position and a needle protecting extended and locked position.

19 Claims, 8 Drawing Sheets

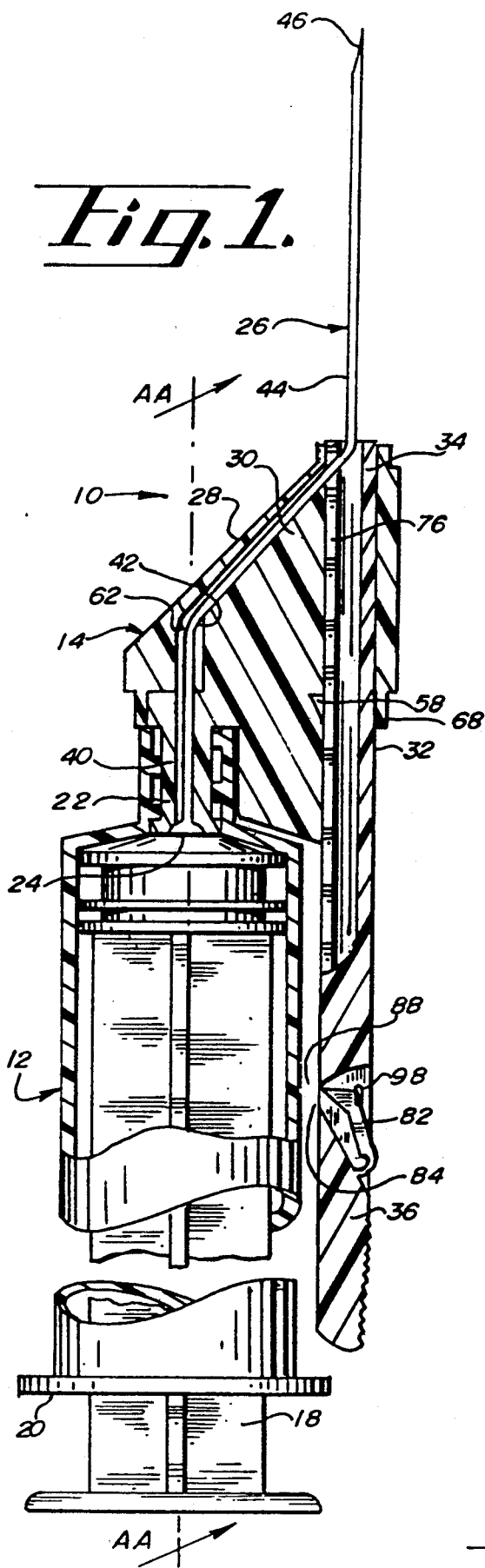
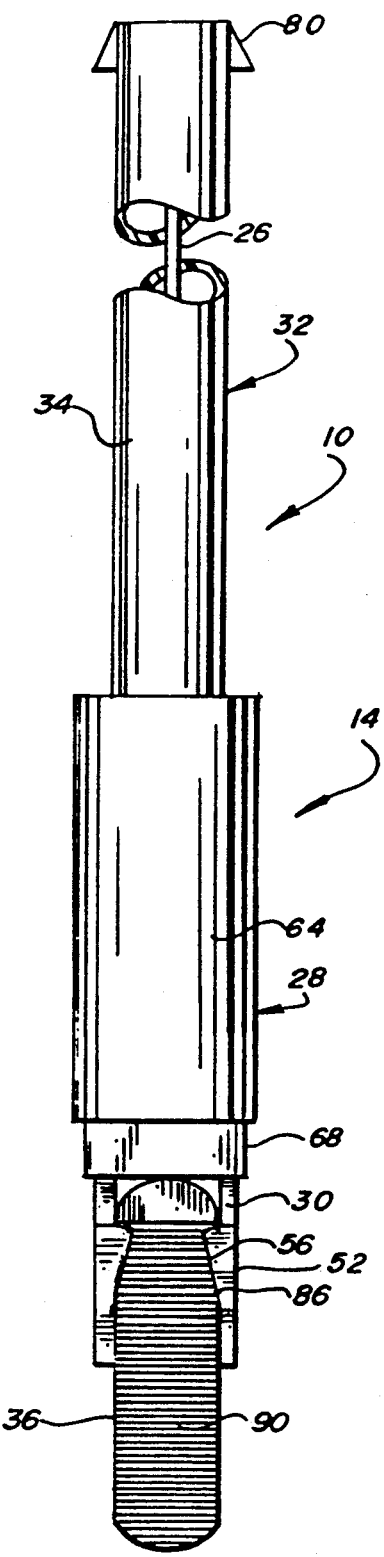

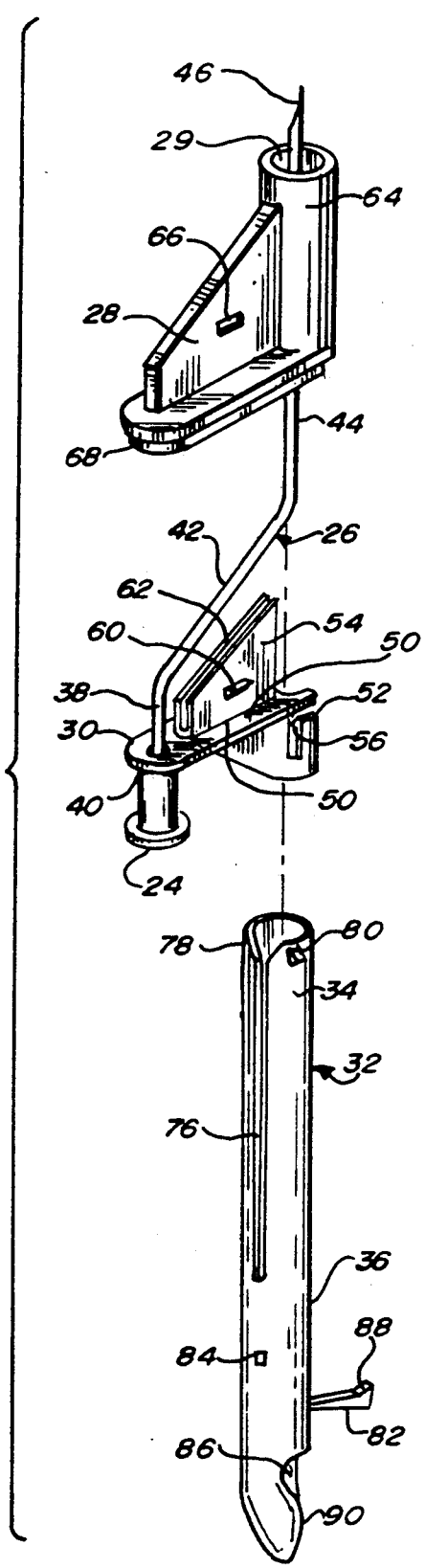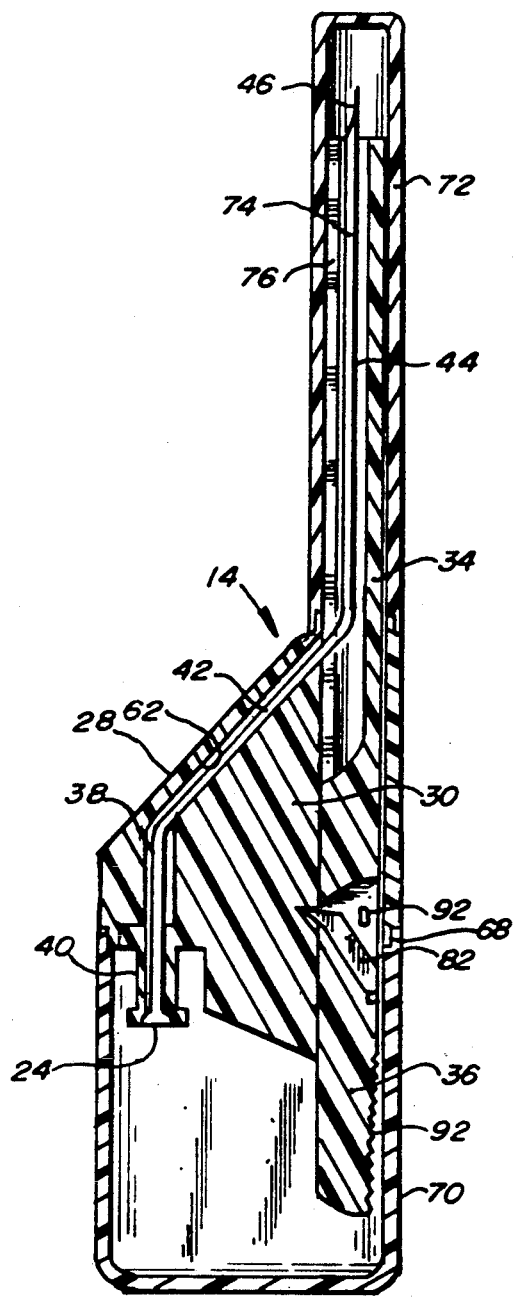

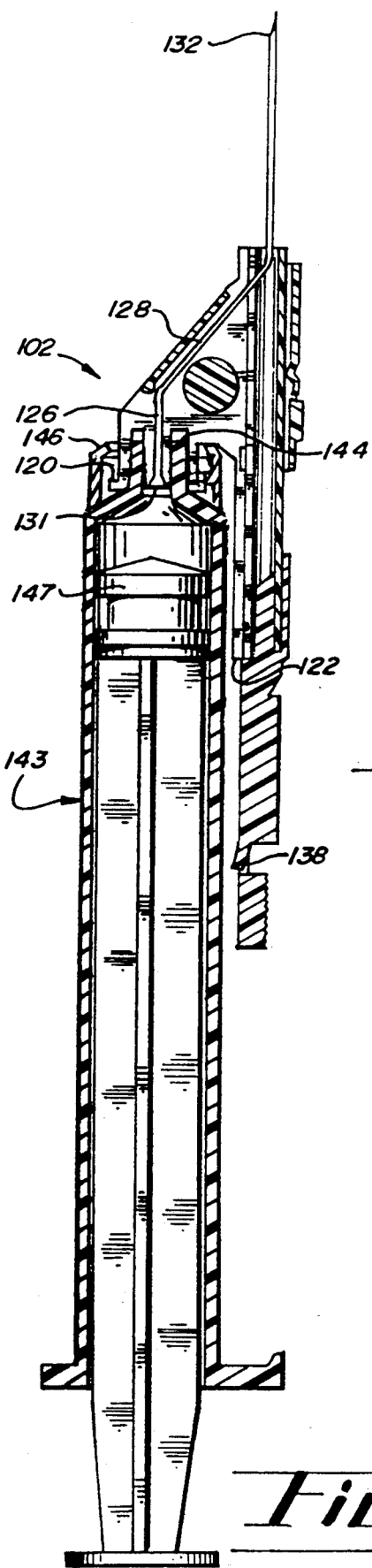
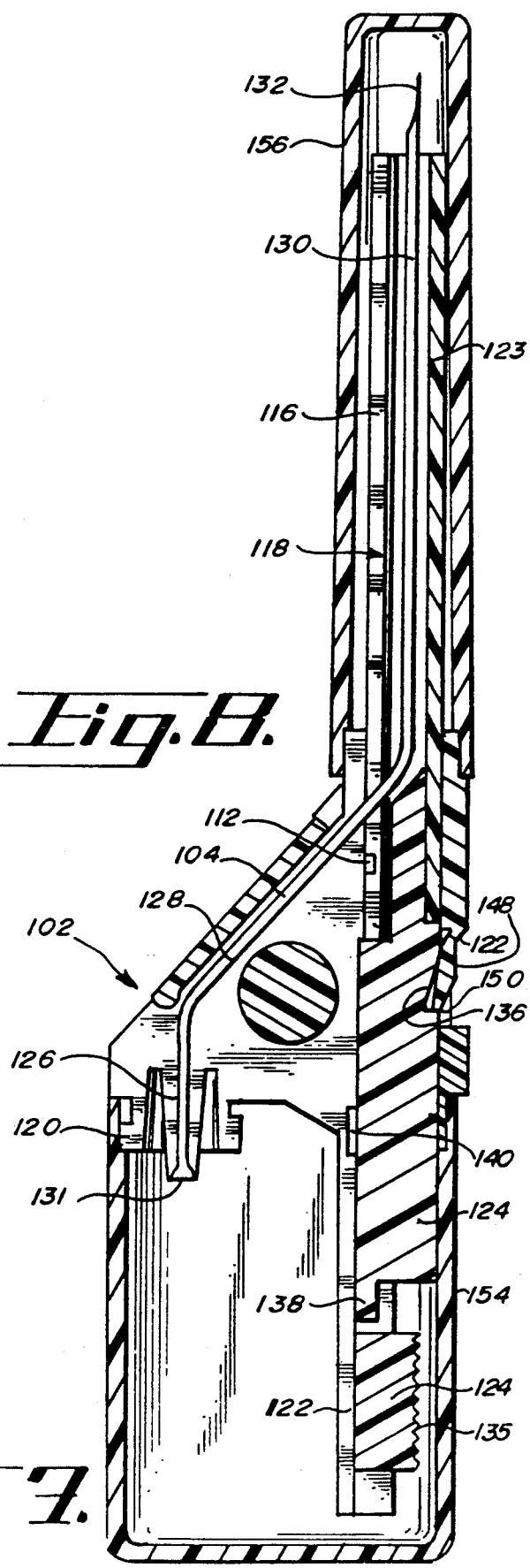
Fig. 7.
Fig. 8.

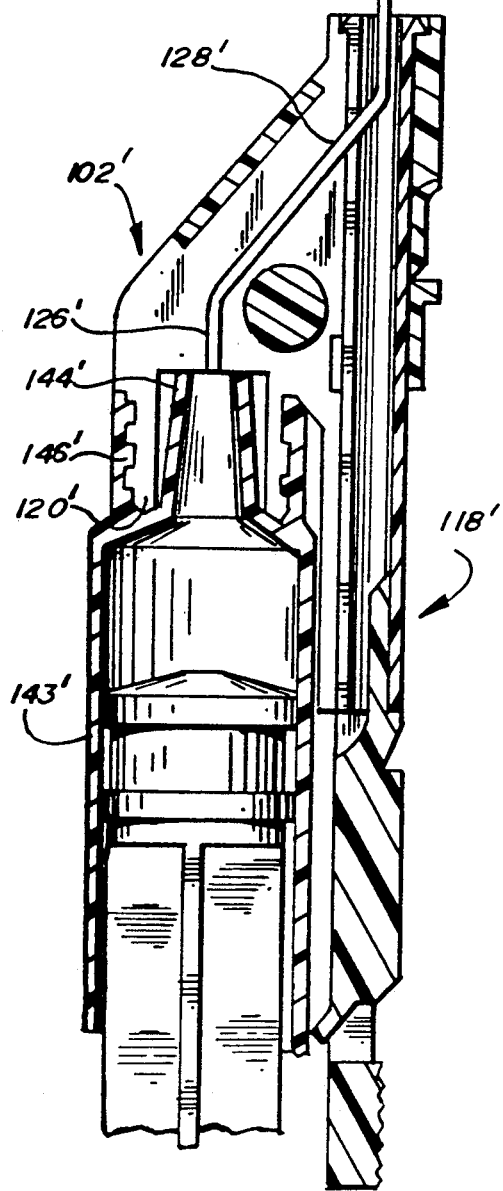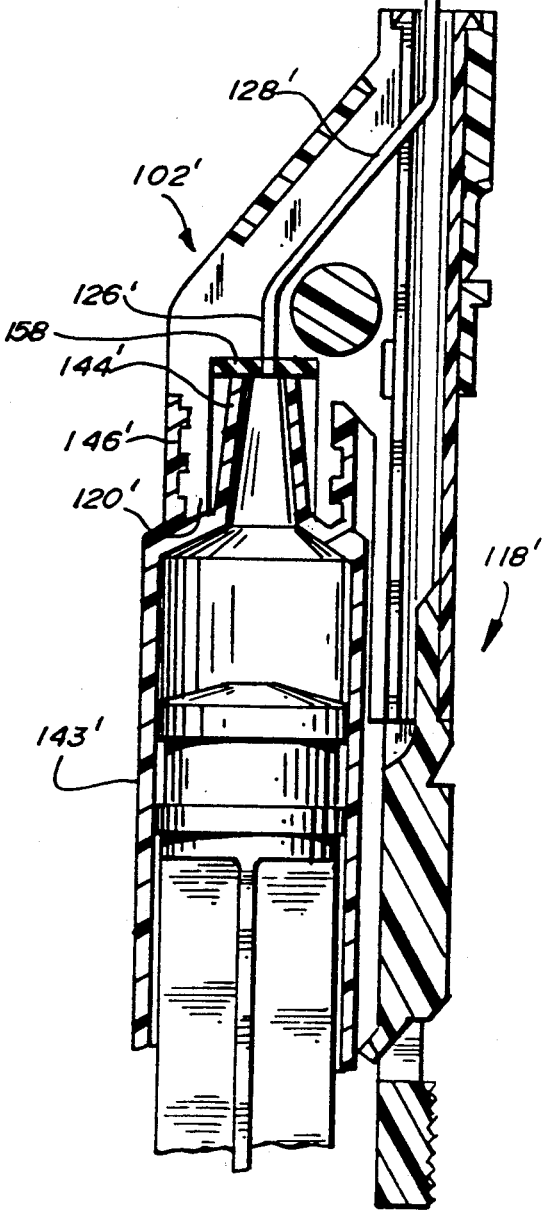

SAFETY SYRINGE WITH OFFSET NEEDLE

This is a continuation of copending application Ser. No. 07/461,603 filed on Jan. 5, 1990, now abandoned.

RELATED APPLICATION

This application is related to copending application filed on Aug. 3, 1989 entitled "Blood Collection Tube Holder Safety Guard" having Ser. No. 07/389,018 now U.S. Pat. No. 5,000,167 which is incorporated herein by reference.

FIELD OF THE INVENTION

This invention relates to syringes and more particularly to a safety syringe having an extendable needle guard thereon for preventing accidental needle sticks.

BACKGROUND OF THE INVENTION

The majority of syringes used today for medical or laboratory purposes are disposable and are intended to be discarded after a single use. Disposal of the syringes poses a potential hazard for the individuals who use the syringes, as well as for those who dispose of them. With the increased awareness concerning the potential for the transmission of AIDS and other infectious diseases, a number of different devices have been proposed to prevent accidental needle sticks or to otherwise disable the syringe after a single use.

One approach to this problem is to provide a protective shield which is movable between a retracted position and an extended position. A common feature of these syringes is that when the retracted shield is moved to the extended position, the shield covers the needle and cannot be retracted without the use of extraordinary force.

A number of such constructions have been proposed to satisfy the general requirement that the needle be permanently covered after the syringe has been used. Some of these constructions involve twist-to-lock mechanisms which often require at least two hands to operate and do not readily indicate when the shield has been locked into the extended position. Other syringes lock automatically when the shield is extended. In many of these syringes, the locking mechanism remains exposed and may be manually manipulated to retract the shield after the shield has been "irreversibly" locked.

Although many of these constructions meet the general requirements for a safety syringe, many of these devices are much too complicated to manufacture economically and efficiently. Certain of these devices require extensive modification of the conventional syringe components. This is generally unacceptable due to the large investment most syringe manufacturers have in their present molding and extrusion equipment. Other devices cannot realistically be mass produced using presently known manufacturing techniques. Finally, certain other devices require a large number of manipulative steps during the assembly process and thus cannot be efficiently mass produced.

Finally, many of the proposed safety syringes require the health care worker to use both hands to perform complex manipulations of the safety syringe in order to move the protective shield to the extended needle protecting position. Typically, the user must hold the syringe barrel with one hand while the other hand is used to move the protective shield distally to the extended position. In certain other constructions, the user must place their hands unacceptably close to the potentially infective needle to move the protective shield to the extended position. In many situations, it is preferable for the user to be able to move the protective shield to an extended and locked position by safely moving their thumb distally along the barrel section of the syringe.

SUMMARY OF THE INVENTION

An object of the present invention is to substantially overcome the disadvantages mentioned above.

Another object of the present invention is to provide a safety syringe which performs all of the general requirements of this type of syringe and which cannot be readily manipulated to defeat the locking mechanism once the protective needle shield assembly is placed in the extended and locked position.

A further object of the present invention is to provide a safety syringe which is inexpensive to manufacture using existing manufacturing methods and equipment.

Another object of the present invention is to provide a safety syringe wherein the protective needle shield assembly may be readily extended or retracted over the distal needle section of the nonlinear needle by moving the finger member section of the needle shield assembly distally or proximally along the barrel of a conventional syringe.

In accordance with one form of the present invention, an integral needle housing is mounted on the distal end of a conventional syringe so that a protective needle shield assembly is generally aligned and movable along a support member positioned on the side of the syringe barrel between retracted and extended positions. The needle housing preferably includes a nonlinear needle fixedly retained therein to provide communication between the interior of the syringe barrel and the injection site of the patient.

The needle housing of this embodiment includes a needle shield assembly consisting generally of a finger member section and a protective shield section wherein the finger member section and the protective shield section are integral and are slidable linearly through a bore in the needle housing between a retracted position wherein the needle point on the distal needle section is exposed and an extended position wherein the needle point is protected. The needle shield assembly also preferably includes a movable start detent that allows the needle shield assembly to be initially moved only in the proximal direction along the distal needle section of the nonlinear needle to expose the distal end of the needle. In the initial start position, the distal needle section of the nonlinear needle is partially protected by the protective shield section of the needle shield assembly. As the needle shield assembly is moved proximally from the initial start position, the start detent is moved from a contacting relation with a recess on the inner side of the bore of the needle housing to a neutralized position wherein the start detent is generally planar with the interior surface of the bore of the needle housing.

When the needle shield assembly is in the fully retracted position, the medication to be injected may be drawn into the syringe in the usual manner. When the medication has been injected into the patient, the distal needle section of the nonlinear needle is withdrawn from the patient and the user may simultaneously move the protective shield to the extended and locked position. Unlike previous safety syringes, the present invention allows the user to hold the syringe barrel and move the protective shield to the extended position by placing their thumb on a ribbed surface located on the finger member section of the shield assembly and moving the ribbed surface distally until the needle shield assembly has been moved to an extended and locked position. Once this occurs, the protective shield section of the needle shield assembly will protect the distal needle section of the nonlinear needle and may not be moved to the retracted position without the use of excessive force.

In another form of the invention described herein, the needle shield assembly is slidable in a nonlinear manner between extended and retracted positions to protect or expose a preferably linear needle.

An advantage of the present invention is that it is relatively inexpensive to manufacture and simple to use.

A further advantage of the present invention is that it offers the user a convenient method of moving the needle shield assembly between retracted and extended positions.

A further advantage of the present invention is that it may be used with a conventional syringe.

A further advantage of the present invention is that the use of a nonlinear needle allows for the convenient alignment of the distal needle point with the desired injection site.

Yet another advantage of the present invention is that it does not require the user to place their hands near the potentially infectious distal needle point in order to move the needle shield assembly to the extended position.

BRIEF DESCRIPTION OF THE DRAWINGS

FIG. 1 is a side elevation view, partially in cross-section and partially cut-away of the preferred embodiment of the present invention shown mounted on a conventional syringe with reference plane A—A and with the needle shield assembly shown in the retracted position;

FIG. 2 is a frontal elevation view partially cutaway, of the preferred embodiment with the needle shield assembly shown in the extended and locked position;

FIG. 3 is an exploded perspective view of the needle housing of the preferred embodiment of the present invention illustrated in FIGS. 1 and 2;

FIG. 4 is a side cross-sectional view of the non-linear needle and the needle housing shown in the assembled condition and with the needle shield assembly shown in the initial start position;

FIG. 7 is a side elevation view partially in cross-section, of the embodiment of the present invention illustrated in FIG. 6 shown mounted on a conventional syringe, portions of which are shown partially in cross-section;

FIG. 8 is a side elevational view partially in cross-section of the embodiment of the present invention illustrated in FIG. 6 with the nonlinear needle and needle housing shown in the assembled condition and with the protective shield shown in the initial start position of the embodiment of the present invention illustrated in FIG. 6;

FIG. 13 is a side elevation view, partially in cross-section and partially cut-away, of an alternate embodiment of the present invention shown mounted on a conventional syringe and with the needle shield assembly shown in the retracted position;

FIG. 14 is a side elevation view, partially in cross-section and partially cut-away, of an alternate embodiment of the present invention shown mounted on a conventional syringe with the needle shield assembly shown in the retracted position;

DETAILED DESCRIPTION OF THE INVENTION

The invention disclosed herein is intended to be used in conjunction with a conventional syringe; however, it is anticipated that the present invention may be modified for use with nearly all needle bearing medical or laboratory devices, without departing from the contemplated scope of the present invention as defined by the claims attached hereto. For example, it is anticipated that the embodiments described herein may be modified to form a safety dental syringe of the type adapted to receive a medication containing cartridge in fluid communication with a conventional threaded dental syringe hub.

Figure 6:
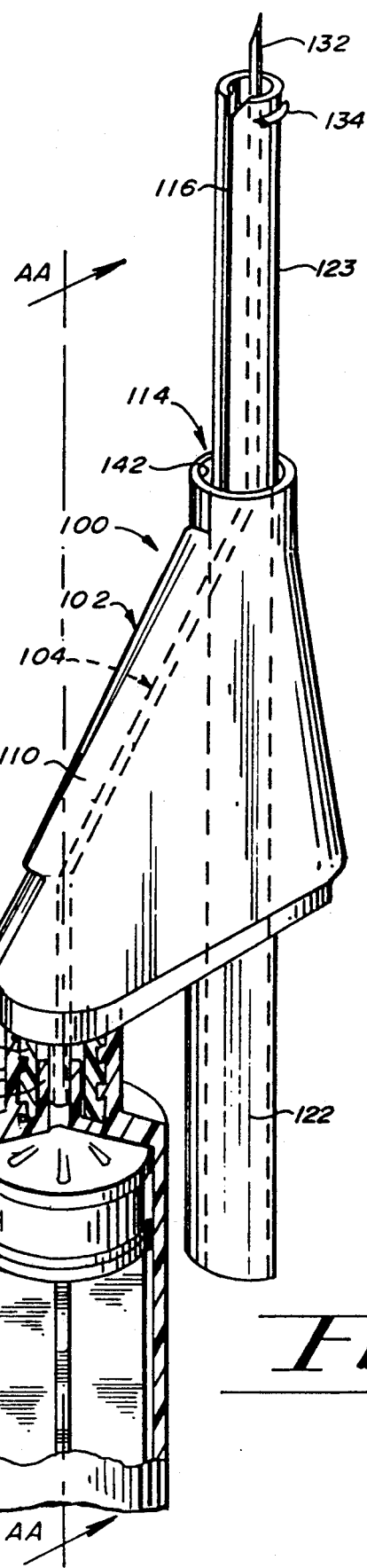
FIG. 6 is a perspective view of an alternate embodiment of the present invention with reference plane A—A and shown mounted on a conventional syringe, portions of which have been cut-away and with the needle shield assembly shown in the initial start position.
Figure 9A:
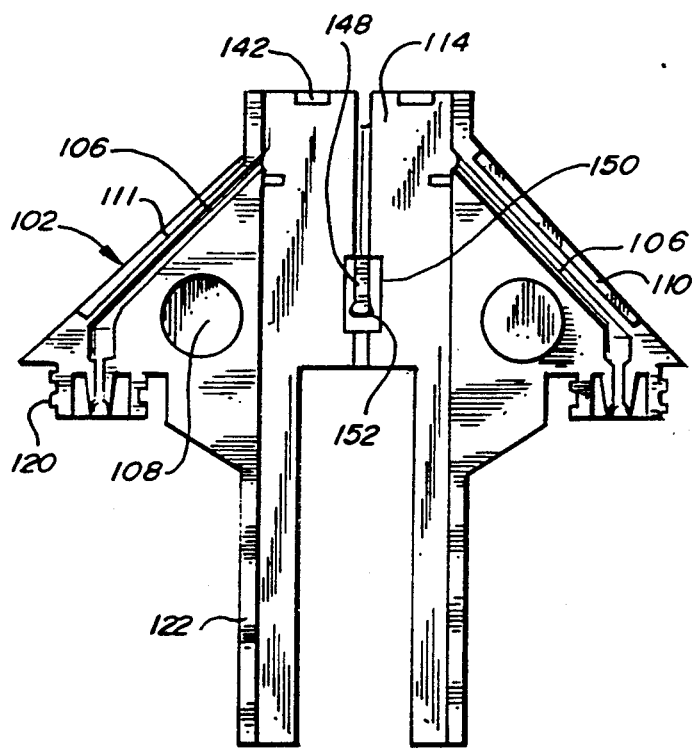
FIG. 9A is a side elevation view of the needle housing of the embodiment of the present invention illustrated in FIG. 6 shown in the unassembled condition prior to folding.
Figure 9B:
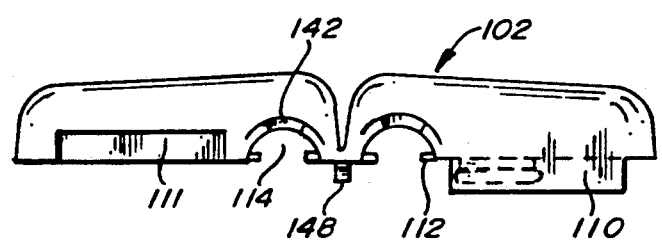
FIG. 9B is a top elevation view of the needle housing of the embodiment of the present invention illustrated in FIG. 9A shown in the unassembled condition prior to folding.
Figure 10:
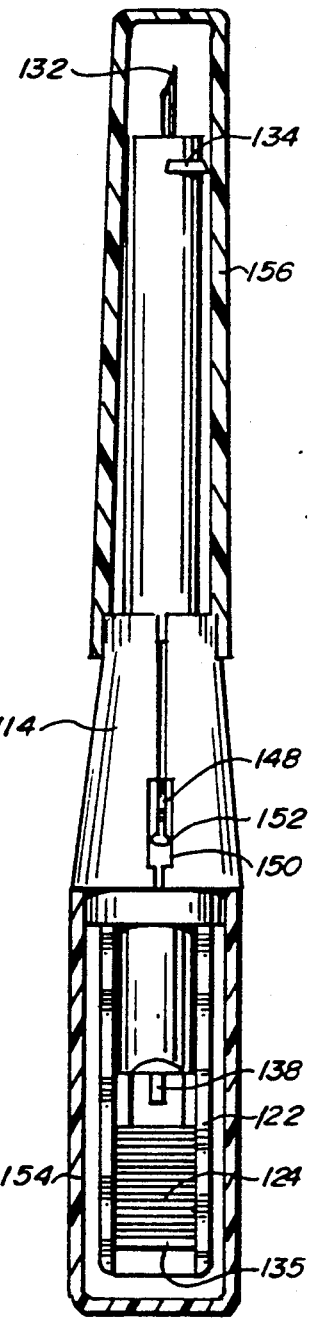
FIG. 10 is a front elevation view, partially in cross-section, of the embodiment of the present invention illustrated in FIG. 6 with the needle shield assembly shown in the initial start position.

In describing the present invention, the term "distal end" of an element refers to the end of the element closest to the needle point of the device which is designed to pierce the skin of the patient. The term "proximal end" of an element refers to the end of the element furthest from the needle point which is designed to pierce the skin of the patient. The terms "inner" or "inwardly" and "outer" and "outwardly" are used herein to refer to the orientation of an element with respect to the reference plane designated as A—A in FIGS. 1 and 6.

As illustrated in the attached drawings, the preferred form of the present invention is adapted to be used with a conventional syringe to provide a safety syringe which 15 referred to herein generally as safety syringe 10. The safety syringe 10 includes a conventional syringe 12 and a needle housing 14. The conventional syringe 12 includes an elongate tubular barrel section 16, a plunger 18 and a proximally located finger flange 20. A cylindrically shaped luer skirt 22 is integrally formed at the distal end of the barrel section 16 of this embodiment to encircle a needle hub section 40 on the needle housing 14. The interior surface of the luer skirt 22 includes internally directed threads adapted to threadedly engage complimentary threads on the proximal end of the needle hub section 40.

In the preferred embodiment of this safety syringe 10, the needle housing 14 consists of a pair of preferably molded elements which may be snap fit or adhesively bonded together to retain an offset or nonlinear hollow needle referred to herein generally as nonlinear needle 26 in a sterile, fixed position substantially within the needle housing 14. The needle housing 14 of this embodiment consists generally of a needle cover 28 which is integral with a needle platform 30 to slidably receive a needle shield assembly 32 in a linear shield bore 29 located along the outer surface of the needle housing 14. The needle shield assembly 32 of this embodiment, preferably includes a distal section described herein as a protective shield section 34 and a proximal section described herein is a finger member section 36, the function of which will be described hereinafter.

The nonlinear needle 26 of this embodiment includes a short hollow proximal needle section 38 which is preferably straight and includes a funnel shaped orifice 24 on the needle hub section 40 to provide fluid communication between the syringe 12 and the needle nonlinear 26. The internal threads on the luer skirt 22 engage the external threads on the needle hub section 40 to retain the needle housing 14 on the distal end of the conventional syringe 12 in a conventional manner. An angularly oriented hollow intermediate needle section 42 of the nonlinear needle 26 is fixedly connected at its proximal end to the distal end of the proximal needle section 38 and the distal end of the proximal needle section 28 extends into the shield bore 29 to a fixed connection with the proximal end of an elongate hollow distal needle section 44. Although the intermediate needle section 42 is illustrated and described herein as being an integral part of the nonlinear needle 26, it is anticipated that a hollow fluid passageway (not shown) may be formed in the needle housing 14 to replace the intermediate needle section 42. The proximal needle section 38 and the distal needle section 44 of the preferred embodiment may then be molded into the needle housing 14 with the fluid passageway therebetween. The distal needle section 44 extends from the shield bore 29 to a location distally beyond the distal end of the needle housing 14. The proximal needle section 38 and the distal needle section 44 of the nonlinear needle 26 are preferably straight needle sections which are interconnected by the angular intermediate needle section 42 to form the overall nonlinear orientation of the nonlinear needle 26. The axes of the proximal needle section 38 and the distal needle section 44 are oriented in a generally parallel and laterally offset manner with respect to each other in order to create the preferred shape of the nonlinear needle 26 and to facilitate the operation of the present invention which will be discussed more fully hereinafter.

As illustrated in FIG. 3, the needle platform 30 of the needle housing 14 in the preferred embodiment is integral with the needle hub section 40, and includes a generally flat platform surface 50 which supports a shield locking section 52 to retain the needle shield assembly 32 in the extended position and an angled positioning surface 54 which fixedly supports the intermediate needle section 42 of the nonlinear needle 26 therein, all of which will be discussed more fully hereinafter. The needle hub section 40 of the needle platform 30 is positioned along the inner proximal side of the flat platform surface 50 and extends proximally from the flat platform surface 50 a sufficient distance to contact and engage the luer skirt 22 of the syringe 12. The shield locking section 52 of the needle platform 30 is preferably a semi-circular extension having a pair of inwardly biased and preferably ramp shaped locking detents 56 on the sides thereof and a wedge shaped start detent recess 58 on the inner surface thereof, the function of which will be discussed hereinafter. The shield locking section 52 extends proximally from the outer side of the flat platform surface 50 to form the inner surface of the shield bore 29 and frictionally contact the inner surface of the shield assembly 32. The angled positioning surface 54 of the needle platform 30 is a quadrilaterally shaped element which extends distally from the top surface of the flat platform surface 50 between the needle hub section 40 and the shield locking section 52. The sides of the angled positioning surface 54 include a pair of perpendicularly extending needle cover retaining tabs 60 thereon. The top surface of the angled positioning surface 54 is angled to match the general angle of the intermediate needle section 42 on the nonlinear needle 26 and further includes a needle groove 62 thereon which cooperates with the inner surface of the needle cover 28 to retain the intermediate needle section 42 immovably within the needle housing 14 once the needle housing 14 is assembled.

The needle cover 28 is preferably a molded element which encloses and retains the intermediate needle section 42 of the nonlinear needle 26 within the needle groove 62. The outer side of the needle cover 28 includes a cylindrical shield support cylinder 64 which slidably encloses and retains the needle shield assembly 32 in the shield bore 29 formed by the shield locking section 52 of the platform surface 50 and the shield support cylinder 64. The sides of the needle cover 28 include a pair of tab retaining slots 66 which irreversibly retain the tabs 60 form the angled positioning surface 54 therein to maintain the needle housing in the assembled condition. A perimeter flange 68 is spaced slightly above the proximal end of the needle cover 28 to provide a support and attachment surface to allow a proximal hard case 70 (FIG. 4) to be heat staked or otherwise attached to the needle cover 28 to maintain the sterility of the needle housing 14 during shipping and storage.

The needle shield assembly 32 of this embodiment is preferably a rigid elongate tubular element consisting of a distal protective shield section 34 and, as shown in FIG. 1, an integral and proximal finger member section 36. As shown in FIG. 3, the protective shield section 34 of the needle shield assembly 32 includes an elongate needle slot 76 extending along the inside surface of the protective shield section 34 through which the distal end of the intermediate needle section 42 of the nonlinear needle 26 projects. The distal end of the needle slot 76 preferably includes a notched section 78 to facilitate the passage of the nonlinear needle 26 into the needle slot 76 during assembly of the needle housing 14. A pair of radial tabs 80 are positioned on and extend outwardly from the distal end of the protective shield section 34 to limit the proximal movement of the needle shield assembly 32 within the shield bore 29 of the needle housing 14.

Figure 5:
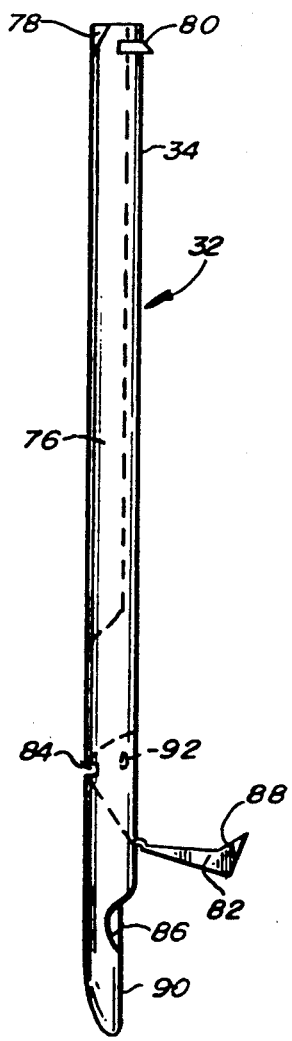
FIG. 5 is a side elevation view of the needle shield assembly of the preferred embodiment of the present invention.

As best illustrated in FIG. 5, the finger member section 36 of the needle shield assembly 32 preferably includes the start detent 82 on the outer surface thereof which interacts with a start detent slot 84 on the inner surface thereof and a pair of shield locking recesses 86 on the inner and side surfaces of the needle shield assembly 32 which interact with the locking detents 56 on the needle housing 14, respectively, the function of which are described hereinafter. The start detent 82 is a generally wedge shaped, movable element having its proximal end hingedly attached to the outer surface of the needle shield assembly 32 and includes an inwardly oriented positioning tab 88 located on the distal end of the start detent 82. The start detent slot 84 is positioned on the inner surface of the shield assembly 32 opposite the positioning tab 88 of the start detent 82. The positioning tab 88 is preferably angled inwardly with respect to the body portion of the start detent 82 to releasibly project through the start detent slot 84 and into the start detent recess 58 on the needle platform 30 in the initial start position of the safety syringe 10, the purpose of which is described hereinafter. The shield locking recesses 86 are positioned proximal to the start detent 82 on the side surfaces of the needle shield assembly 32 and form a pair of generally wedge shaped recesses the function of which are described hereinafter. The outer surface of the proximal end of the finger member section 36 includes a ribbed surface 90 which is adapted to be gripped by the user to facilitate operation of the preferred embodiment which is described hereinafter.

Assembly of the preferred embodiment is relatively simple and may be accomplished quickly and inexpensively. As illustrated in FIG. 3, the proximal needle section 38 of the nonlinear needle 26 is initially inserted into the needle hub section 40 so that the intermediate needle section 42 of the nonlinear needle 26 oriented to fit within the needle groove 62 on angled positioning surface 54 of the needle platform 30. The nonlinear needle 26 may then be adhesively bonded or welded to any convenient surface on the needle platform 30 to retain the nonlinear needle 26 fixedly thereon. Alternatively, it is anticipated that the nonlinear needle 26 may be molded into the needle platform 30 during the initial molding of the needle platform 30 to ensure a fluid tight fit between the proximal needle section 38 of the nonlinear needle 26 and the needle platform 30. The needle cover 28 is then snapped onto the needle platform 30 by inserting the retaining tabs 60 located on the sides of the angled positioning surface 54 of the needle platform 30 through the tab retaining slots 66 on the needle cover 28 to irreversibly retain the needle cover 28 on the needle platform 30 and so that the distal needle section 44 of the nonlinear needle 26 extends through the shield bore 29 formed by the shield locking section 52 of the needle platform 30 and the shield support cylinder 64 of the needle cover 28.

Once the components of the needle housing 14 are assembled, the start detent 82 is pressed inwardly through the interior of the protective shield section 34 while the needle shield assembly 32 is moved distally through the shield bore 29. The needle shield assembly 32 slides distally through the shield bore 29 until the positioning tab 88 on the start detent 82 passes through the start detent slot 84 and contacts the wedge shaped start detent recess 58 located on the shield locking section 52 of the needle platform 30. In this position, the protective shield section 34 of the needle shield assembly 32 partially encloses the distal needle section 44 of the nonlinear needle 26 and is prevented from further distal movement by contact between the distal end of the positioning tab 88 on the start detent 82 and the distal side of the start detent recess 58. Finally, the proximal hard case 70 is heat staked to the perimeter flange 68 on the needle cover 28 and a distal hard case 72 (FIG. 4) is heat staked to the distal end of the shield support cylinder 64.

In use, when a user desires to inject a medication into a patient using the present invention, the user initially applies lateral pressure to the proximal hard case 70 to break the heat stake between the proximal hard case 70 and the perimeter flange 68 of the needle cover 28. Next, the needle housing 14 is threaded onto a conventional syringe 12 by threading the needle hub section 40 of the needle housing 14 onto the internally threaded luer skirt 22 until the needle hub section 40 forms a fluid tight seal with the distal end of the syringe barrel 16 and the luer skirt 22. Next, the user may remove the distal hard case 72 from the needle housing 14 by rotating the distal hard case 72 until the heat stake on the shield support cylinder 64 is broken.

The user will then move the needle shield assembly 32 from the initial start position (FIG. 4) to a retracted position (FIG. 1) wherein the distal needle section 44 of the nonlinear needle 26 is exposed and the proximal end of the protective shield section 34 extends beyond the proximal end of the needle housing 14. The user may move the needle shield assembly 32 from the initial start position to the retracted position single handedly by placing their thumb on the ribbed surface 90 of the finger member section 36 to move the finger member section 36 proximally through the shield bore 29 until the radial tabs 80 on the distal end of the needle shield assembly 32 contact the shield support cylinder 64. As the needle shield assembly 32 is moved proximally through the shield bore 29, the needle shield assembly 32 and the needle slot 76 are moved proximally over the distal end of the intermediate needle section 42 adjacent to the distal needle section 44 of the nonlinear needle 26. Additionally, as the needle shield assembly 32 is moved proximally through the shield bore 29, the start detent 82 on the needle shield assembly 32 is moved from the start detent recess 58 on the shield locking section 52 of the needle platform 30 and from the start detent slot 84 on the needle shield assembly 32 to a neutralized position within the protective shield section 34 of the needle shield assembly 32 by contact with a pair of supplemental bumps 92 (FIG. 4) which project inwardly into the interior surface of the protective shield section 34 to prevent the start detent 82 from inadvertently returning to the initial start position. Once the shield assembly 32 is moved to the retracted position, the desired medication for injection may be drawn into the syringe 12 by withdrawing the plunger 18 in the same manner as with any conventional syringe 12.

Next, a bevelled distal needle point 46 on the distal needle section 44 may be aligned with the appropriate injection site to inject the medication into the patient.

The distal needle point 46 on the distal needle section 44 is oriented so that when the bevel of the distal needle point 46 is aligned to pierce the skin of a patient, the safety syringe 10 will be aligned parallel to the patient's arm when the safety syringe 10 is used to give an intravenous injection. Once the injection has been given and the distal needle section 44 of the nonlinear needle 26 has been removed from the patient, the user may hold the safety syringe 10 of the present invention in one hand and move the finger member section 36 of the needle shield assembly 33 distally through the shield bore 29 until the protective shield section 34 of the needle shield assembly 32 encloses the distal needle section 44 and distal needle point 46 of the nonlinear needle 26. As the needle shield assembly 32 moves distally through the shield, the ramped surfaces of the locking detents 56 of the flat platform surface 50 will be biased against the sides of the needle shield assembly 32 until the locking detents 56 reach the shield locking recesses 86 on the finger member section 36 of the needle shield assembly 32. When the needle shield assembly 32 is in the extended and locked position (FIG. 2), the cooperation between the locking detents 56 and the shield locking recesses 86 will prevent the needle shield assembly 32 from being retracted unless excessive force is applied to the needle shield assembly 32.

Another form of the present invention is illustrated in FIGS. 6-12. The needle housing 102 of this embodiment preferably consists of a foldable, one-piece molded element which may be molded as illustrated in FIGS. 9A and 9B and then folded and bonded around the hollow nonlinear needle referred to herein generally as nonlinear needle 104 to form the assembled needle housing 102 illustrated in FIG. 6. It is anticipated that the needle housing 102 may alternatively be formed by a pair of molded elements which are then bonded together to retain the nonlinear needle 104 therein. The needle housing 102 as illustrated in FIGS. 9A and 9B, includes a needle recess 106, a bonding surface 108, a needle protecting lip 110 and a shield alignment lip 112 all of which are described hereinafter. The needle recess 106 comprises an elongate channel in the assembled needle housing 102 which is formed by a pair of elongate grooves located near the top surface of each half of the needle housing 102 to fixedly retain a substantial portion of the nonlinear needle 104 in the needle housing 102. The bonding surface 108 consists of a protrusion on one of the halves of the needle housing 102 and a complementary recess on the other half of the needle housing 102 which may be adhesively bonded together to irreversibly retain the needle housing 102 in the assembled position. The needle protecting (FIG. 9B) lip 110 consists of an outwardly extending lip which extends outwardly from the top of one half of the needle housing 102 in an overlapping manner into a corresponding recess 111 (FIG. 9B) on the opposing half of the needle housing 102 to maintain the sterility of the nonlinear needle 104 and to prevent access to the needle 104 once the needle housing 102 is assembled. The shield alignment lip 112 consists of a projection which extends into a shield bore 114 located adjacent to the outer side of the needle housing 102 to contact an elongate slit 116 on a needle shield assembly 118 to prevent rotational movement of the needle shield assembly 118 within the shield bore 114 as the needle shield assembly 118 is moved between the retracted and extended positions, the structure and function of which are described hereinafter.

The assembled needle housing 102 preferably includes the nonlinear needle 104 which is fixedly retained within a proximally located needle hub section 120 and a shield support member 122 which consists of an elongate member which extends from the proximal side of the needle housing 102 in alignment with the shield bore 114 to support the needle shield assembly 118 as the needle shield assembly is moved between the retracted and extended positions described hereinafter. As with the preferred embodiment, the nonlinear needle 104 of the present embodiment consists generally of a hollow proximal needle section 126, a hollow intermediate needle section 128 and a hollow distal needle section 130. The proximal needle section 126 extends proximally from the curved intermediate needle section 128 within the needle recess 106 to the proximal end of a funnel-shaped orifice 119 in the needle hub section 120 of the needle housing 102 to provide fluid communication between the luer skirt 146 and a luer tip 144 of a conventional syringe 143 (FIG. 7) and the distal needle section 130. The intermediate needle section 128 and the proximal needle section 126 are positioned within the needle housing 102 to form the protected and enclosed portion of the nonlinear needle 104. The distal needle section 130 of the nonlinear needle 104 is preferably straight and extends from the distal end of the intermediate needle section 128 in the shield bore 114 to a distal needle point 132 which projects distally beyond the distal end of the needle housing 102. As in the preferred embodiment, the bevelled distal needle point 132 is particularly oriented to facilitate the insertion of the distal needle section 130 of the nonlinear needle 104 when the user injects a medication intravenously into a patient. Additionally, the axes of the proximal needle section 126 and the distal needle section 130 of the nonlinear needle 104 are preferably oriented in a generally parallel and offset manner with respect to each other to facilitate the user's movement of the needle shield assembly 118 between the retracted and extended positions described hereinafter.

The needle shield assembly 118 of the present embodiment preferably consists of a distal protective shield section 123 and a proximal finger member section 124 which form an elongate tubular member constructed of a semi-rigid polypropylene having sufficient rigidity to protect against being accidentally deflected off the distal needle section 130 of the nonlinear needle 104 by the user while having sufficient flexibility to be positioned along the distal needle section 130 so that the sides of the needle shield assembly adjacent to the elongate slit 116 are oriented in an overlapping or encircling manner along the lengthwise dimension of the distal needle section 130 of the nonlinear needle 104. The elongate slit 116 of the needle shield assembly 118 extends proximally from the distal end of the protective shield section 123 to a location approximately midway along the needle shield assembly 118. A pair of radial tabs 134 extend radially outwardly from a location near the distal end of the needle shield assembly 118 adjacent to the distal end of the elongate slit 116 to limit the proximal movement of the needle shield assembly 122 within the shield bore 114. The proximal end of the needle shield assembly 118 includes a ribbed finger member 135 on the proximal end of the finger member section 124, the function of which is described hereinafter. The protective shield section 123 and the finger member section 124 of the needle shield assembly 118 are slidably retained in the shield support member 122 and are preferably oriented to be movable through the shield bore 114 and in the shield support member 122 which is positioned adjacent to the outer side of the barrel section 16 of the conventional syringe 12 when the safety syringe 100 of the present embodiment is assembled. Although the needle shield assembly 118 is preferably constructed as a two-piece molded or extruded element wherein the protective shield section 123 and the finger member section 124 are formed as separate elements, it is anticipated that the needle shield assembly 118 may be formed as a single-piece molded or extruded element.

Figures 11, 12:
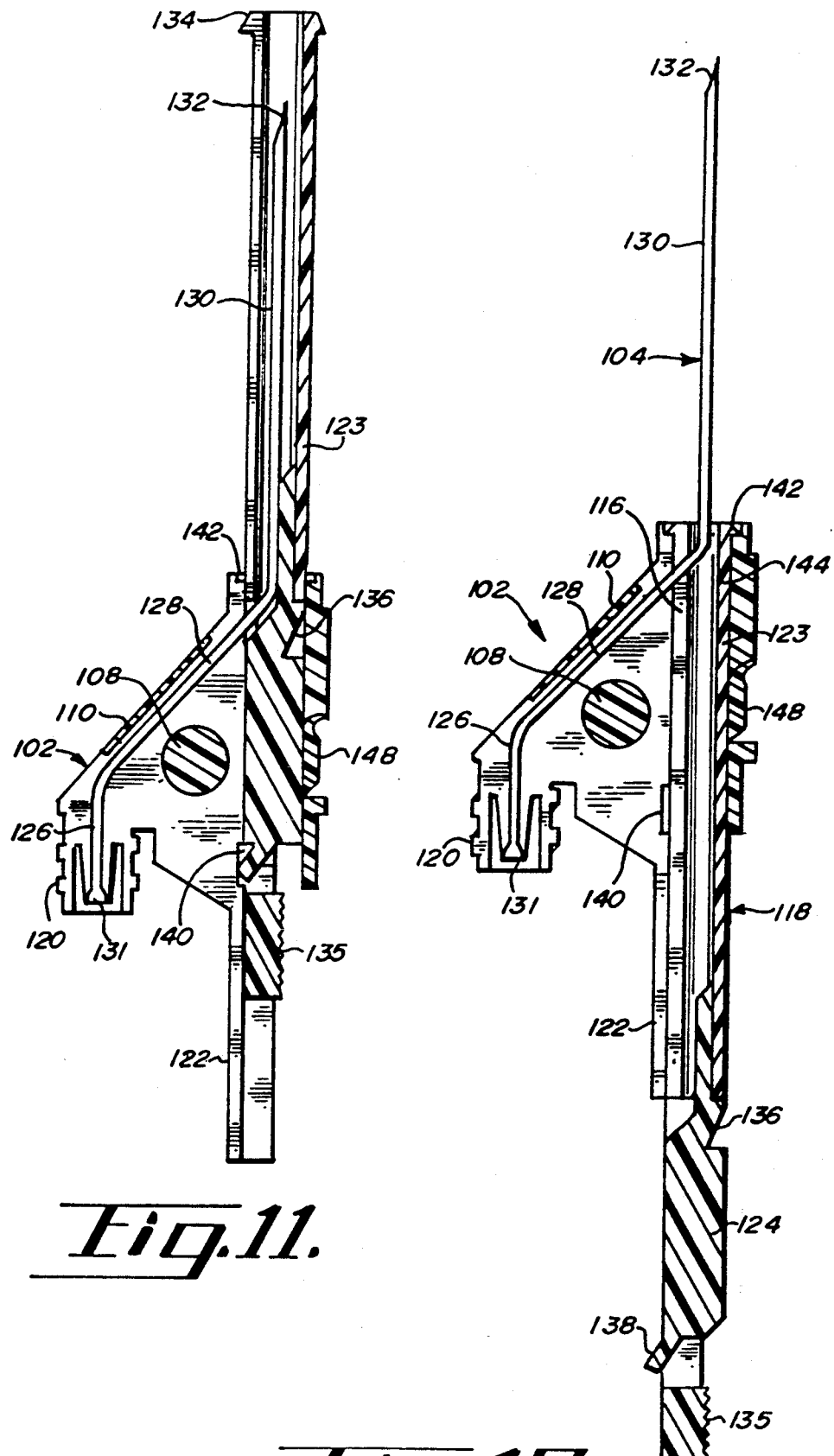
FIG. 11 is a side elevation view, partially in cross-section, of the embodiment of the present invention illustrated in FIG. 6 with the needle shield assembly shown in the extended and locked position.
FIG. 12 is a side elevation view, partially in cross-section of the embodiment of the present invention illustrated in FIG. 6 with the needle shield assembly shown in the retracted position.

FIGS. 11 and 12 of this embodiment illustrate the needle shield assembly 118 in the extended and retracted positions, respectively. The needle shield assembly 118 includes a generally wedge-shaped start detent recess 136 positioned on the outer side of the needle shield assembly 118 adjacent to the proximal end of the protective shield section 123, the function of which is described hereinafter. An inwardly biased locking tab 138 is positioned on the inner surface of the needle shield assembly 118 near the proximal end of the finger member section 124 adjacent to the ribbed member 135. The locking tab 138 is biased inwardly from the finger member section 124 to form a contacting relation with a locking recess 140 located on the inner side surface of the shield bore 114, the function of which is described hereinafter.

The shield support member 122 of the needle housing 102 includes an elongate semicircular groove or channel along the outer side of the proximal end of the needle housing 102 to support the inner side portion of the needle shield assembly 118 therein. The distal end of the needle housing 102 includes an enlarged recess 142 thereon adjacent to the distal end of the shield bore 114 to releaseably retain the radial tabs 134 on the needle shield assembly 118 when the needle shield assembly 118 is in the retracted position described more fully hereinafter. The shield alignment lip 112 extends into the enclosed shield bore 114 to contact the elongate slit 116 on the needle shield assembly 118 to prevent rotational movement of the needle shield assembly 118 within the shield bore 114. The outer side surface of the needle housing 102 includes the start detent 148 located in the side recess 150 (FIG. 9A) on the needle housing 102. The start detent 148 is aligned to project into the shield bore 114 to contact the start detent recess 136 on the needle shield assembly 118 when the needle shield assembly 118 is in the initial start position described more fully hereinafter. The proximal end of the start detent 148 preferably includes a pair of contacting lips 152 (FIG. 9A) to frictionally contact the sides of the side recess 150 to retain the start detent 148 in a neutralized position once the needle shield assembly 118 is moved proximally from the initial start position.

FIG. 8 illustrates the present embodiment assembled for shipping and storage. The proximal end of the needle housing 102 preferably includes a rectangularly shaped proximal hard case 154 which is heat staked or bonded to the proximal end of the needle housing 102. The proximal hard case 154 protects the proximal end of the needle housing 102 and maintains the sterility of the proximal end of the needle housing 102 and the needle shield assembly 118 during shipping and storage of the present embodiment. The distal end of the safety syringe 100 includes an elongate tubular distal hard case 156 thereon. The distal hard case 156 is preferably heat staked to the distal end of the needle housing 102. The distal hard case 156 protects the distal end of the needle housing 102 and maintains the sterility of the distal needle section 130 of the nonlinear needle 104 and the protective shield section 123 of the needle shield assembly 118 during shipping and storage of the present embodiment.

In operation, when the health care worker desires to inject a medication into a patient using the present embodiment, the user initially applies lateral pressure to the proximal hard case 154 to break the heat stake on the proximal end of the needle housing 102. Next, the needle housing 102 is threaded onto the distal end of a conventional syringe 143 so that the luer tip 144 and luer lock skirt 146 of the conventional syringe 143 contact the needle hub section 120 of the needle housing 102 to form a fluid tight seal therebetween. Once the medication to be injected has been prepared, the user may then remove the distal hard case 156 from the needle housing 102 by rotating the distal hard case 156 until the heat stake on the distal end of the needle housing 102 is broken.

Next, the user may move the needle shield assembly 118 from the initial start position (FIG. 8) wherein the protective shield section 123 of the needle shield assembly 118 substantially protects the distal needle section 130 of the nonlinear needle to a retracted position (FIG. 7) wherein the distal needle section 130 is exposed. As with the preferred embodiment, the user may move the needle shield assembly 118 of this embodiment to the retracted position by placing their thumb on the ribbed member 135 to move the finger member section 124 of the needle shield assembly proximally through the shield bore 114 until the distal needle section 130 of the nonlinear needle is exposed by the protective shield section 123 of the needle shield assembly 118. As the needle shield assembly 118 is moved proximally through the shield bore 114 of the needle housing 102, the elongate slit 116 on the protective shield section 123 of the needle shield assembly 118 is moved over the distal end of the intermediate needle section 128 and the proximal end of the distal needle section 130. The shield alignment lip 112 on the needle housing 102 extends into the elongate slit 116 of the needle shield assembly 118 to maintain the proper alignment of the needle shield assembly 118 within the shield bore 114. During the proximal movement of the needle shield assembly 118, the start detent 148 is moved from the initial start position (FIG. 8) in the start detent recess 136 to a neutralized position (FIG. 12) wherein the contacting lips 152 of the start detent 148 frictionally contact the sides of the side recess 150 to maintain the start detent 148 planar with the interior surface of the shield bore 114 so that the start detent 148 does not interfere with any further movement of the needle shield assembly 118 in the shield bore 114. The needle shield assembly 118 is moved proximally in the shield support member 114 until the radial tabs 134 on the distal end of the needle shield assembly 118 contact the enlarged recess 142 on the distal end of the needle housing 102. The contact between the radial tabs 134 on the distal end of the needle shield assembly 118 and the enlarged recess 142 of the needle housing 102 prevents further proximal movement of the shield assembly 118 in the shield bore 114. When the needle shield assembly 118 is in the retracted position (FIG. 7), the plunger 147 of the conventional syringe 143 may be retracted in the usual manner to fill the conventional syringe 143 with the medication to be injected. When the conventional syringe 143 has been filled with the medication to be injected, the distal needle section 130 and the distal needle point 132 of the nonlinear needle 104 may be aligned with the intravenous injection site on the patient so that the conventional syringe 143 is aligned parallel the vein of the patient, the distal point 132 will be aligned to pierce the skin of the patient.

After the injection has been given, the user may remove the distal needle section 130 of the nonlinear needle 104 from the patient and immediately move the ribbed member 135 distally along the shield support member 122 until the protective shield section 123 of the needle shield assembly 118 encloses the distal needle section 130 and the distal needle point 132 of the nonlinear needle 104. As the ribbed member 135 and the protective shield section 123 are moved distally along the shield support member 122, the inwardly biased locking tab 138 on the finger member section 124 will frictionally contact the inner surface of the shield support member 122 until the locking tab 138 reaches the locking recess 140 located on the inner surface of the shield support member 122. The locking recess 140 is positioned on the inner surface of the shield bore 114 and adjacent to the distal end of the shield support member 122 so that when the locking tab 138 reaches the locking recess 140, the protective shield section 123 of the needle shield assembly 118 will be protecting the distal needle section 130 and distal needle point 132 of the nonlinear needle 104. The locking tab 138 and the locking recess 140 are also located in an enclosed portion of the shield bore 114 of the needle housing 102 to limit access to the locking mechanism of the present invention.

FIGS. 13 and 14 illustrate yet another form of the present invention particularly adapted to fit a conventional syringe 143 having enlarged internal threads on the luer skirt 146' of the conventional syringe 143'. The embodiments illustrated in FIGS. 13 and 14 include a locking mechanism similar to the locking mechanism described above and illustrated in FIGS. 6-12. The needle hub section 120' of the embodiment illustrated in FIG. 13 forms a fluid tight seal with the luer tip 144' when the needle housing 102' is threaded onto the distal end of the conventional syringe 143'. The internal threads on the luer skirt 146' and the external threads on the needle hub section 120' are oriented so that the needle housing 102' may be threaded onto the distal end of the conventional syringe 143' until the distal end of the luer tip 144' frictionally seals against the needle housing 102' so that the nonlinear needle 104' is in fluid tight communication with the conventional syringe 143'.

FIG. 14 illustrates a further embodiment similar to the embodiment illustrated in FIG. 13 and which includes a sealing member 158. The sealing member 158 of this embodiment is preferably compressed by the distal end of the luer skirt 146' as the needle housing 102' is threaded onto the distal end of the conventional syringe 143' so that a fluid tight seal is formed therebetween. The sealing member 158 also creates frictional resistance to the rotational movement of the needle housing 102' about the conventional syringe 143' so that the seal between the needle housing 102' and the luer skirt 146' will not begin to leak as the user manipulates the assembly prior to injecting the medication into the patient.

Figure 15:
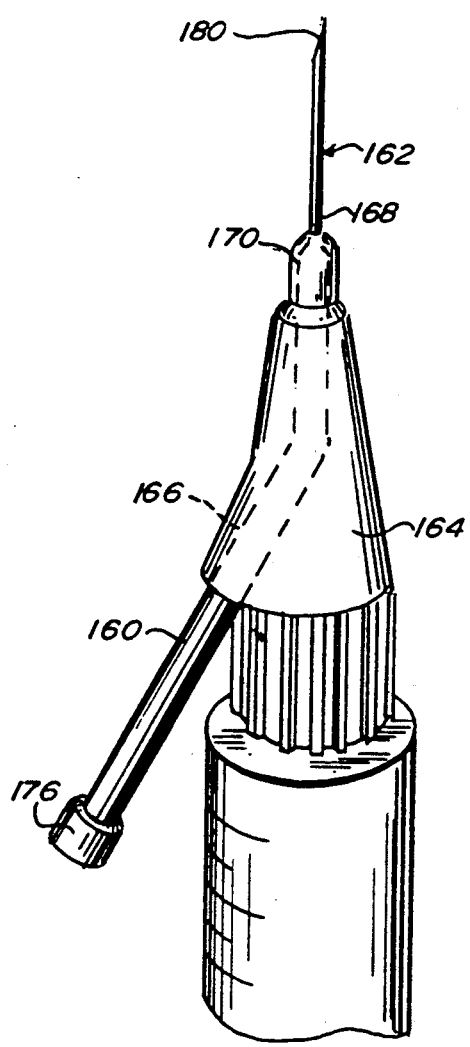
FIG. 15 is a perspective view, partially cut-away, of an alternate embodiment of the present invention shown mounted on a conventional syringe with the needle shield assembly shown in the retracted position.
Figure 16:
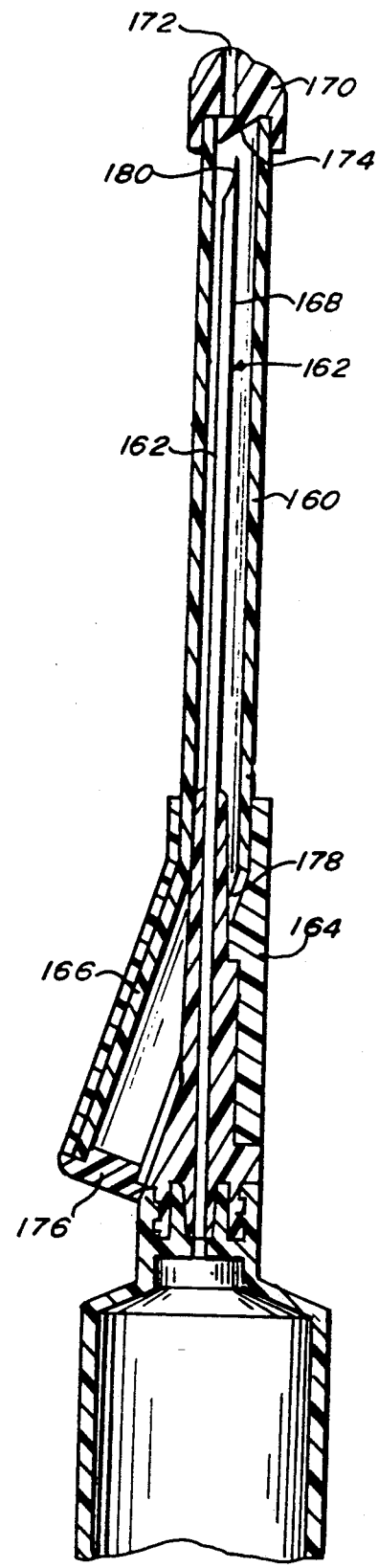
FIG. 16 is a side view, partially in cross-section, of the alternate embodiment of the present invention illustrated in FIG. 15 shown mounted on a conventional syringe with the needle shield assembly shown in the extended position.

FIGS. 15 and 16 illustrate yet another form of the present invention wherein a needle shield assembly 160 is slidable in a nonlinear manner along a hollow and preferably linear needle 162. In this embodiment, a needle housing 164 is preferably threaded onto a conventional syringe 165 of the type described above with respect to the previous embodiments of the present invention. It is anticipated that the needle housing 164 may be formed as an integral part of the distal end of a syringe without substantial modification thereto. The needle housing 164 includes an offset and nonlinear shield passageway 166 through which the needle shield assembly 160 is moved between the retracted and extended positions described hereinafter. The distal end of the needle housing 164 preferably includes a reduced diameter section (not shown) to compress the needle shield assembly 160 as the needle shield assembly 160 passes from the shield passageway 166 onto the distal needle section 168 of the needle 162.

The needle shield assembly 160 of the present embodiment is preferably constructed of a semi-rigid polypropylene having sufficient rigidity to adequately protect the needle 162 in the extended position (FIG. 16) while having sufficient flexibility to pass nonlinearly through the shield passageway 166 and onto the needle 162. The distal end of the needle shield assembly 160 includes a hardened distal tip member 170 to protect the user from accidental needle sticks when the needle shield assembly 160 is in the extended position. As illustrated in FIG. 16, the tip member 170 includes a needle hole 172 centrally located therein to allow the needle 162 to pass therethrough and a flexible lip 174 on the proximal side of the tip member 170 to retain the distal needle section 168 of the needle 162 within the needle shield assembly 160 when the needle shield assembly 160 is in the extended position. The proximal end of the needle shield assembly 160 preferably includes a hardened finger member 176 to facilitate the movement of the protective shield 160 between the retracted (FIG. 15) and extended positions (FIG. 16). An elongate slit 178 extends between the distal and proximal ends of the needle shield assembly 160 to allow the needle shield assembly 160 to pass over the proximal end of the distal needle section 168 as the needle shield assembly 160 is moved between the retracted (FIG. 15) and extended positions (FIG. 16).

When the needle shield assembly 160 is in the retracted position, the tip member 170 is positioned on the proximal end of the distal needle section 168 immediately adjacent to the distal end of the needle housing 164. In this position, the finger member 176 extends proximally from the proximal side of the shield passageway 166 to allow the needle shield assembly 160 to be readily movable to the extended position by merely pressing on the finger member 176 to move the needle shield assembly 160 distally through the shield passageway 166. As the needle shield assembly 160 is moved to the extended position, the tip member 170 moves distally along the distal needle section 168 and the elongate slit 178 is opened as it passes from the shield passageway 166 over the proximal end of the distal needle section 168. Once the elongate slit 178 passes over the proximal end of the distal needle section 168, the reduced diameter section (not shown) of the needle housing 164 compresses the elongate slit 178 to cause the sides of the needle shield assembly 160 to overlap once they have passed beyond the distal end of the needle housing 164.

In the extended position, the tip member 170 extends beyond the distal needle point 180 of the distal needle section 168 a sufficient distance to allow the flexible lip 174 to resiliently cover the needle hole 172 and prevent the distal needle point 180 from returning through the needle hole 172. In the extended position, the finger member 176 on the proximal end of the needle shield assembly 160 is positioned adjacent to the proximal end of the shield passageway 166 and cannot be retracted unless extraordinary force is used to force the distal needle point 180 through the flexible lip 174 and into the needle hole 172 of the tip member 170.

The foregoing is intended to be descriptive of the preferred form of the embodiments described above. It should be understood that certain features of the above-described embodiments are interchangeable or may be modified without departing from the scope of the present invention which is defined by the following claims.

What is claimed is:

1. A medical device comprising:
   a syringe assembly having an elongate barrel section, a distal end and a plunger member slidably received therein;
   an elongate needle means operatively associated with said barrel section and having a distal needle section and a skin piercing needle point,
   a protective shield means slidably mounted adjacent to the syringe and longitudinally movable in use between a retracted position wherein said needle pint is exposed and said protective shield means is laterally substantially separated from said barrel section and an extended position wherein said needle point and said distal needle section are substantially enclosed by said protective shield means, and
   one of said needle means or shield means having an elongate first portion having a first longitudinal axis and an elongate second portion having a second longitudinal axis wherein said first and second longitudinal axes are oriented laterally offset from each other.

2. The medical device of claim 1 further including a locking means thereon to retain said protective shield means in the extended position.

3. The medical device of claim 1 wherein said protective shield means is moveable along at least a portion of said needle means between the retracted and extended positions.

4. The medical device of claim 1 wherein said needle means and said shield means are mountable along said distal end of said syringe assembly.

5. The medical device of claim 4 wherein said shield means includes a proximal first portion oriented in a nonlinear manner with respect to said needle means and a distal second portion adapted to be moveable along said needle means between a retracted and extended position.

6. A medical device particularly adapted for use on a syringe, the medical device comprising:
   an elongate needle means having a skin piercing needle point,
   a protective shield means adapted to be slidably mounted adjacent to the syringe to be moveable from a retracted position wherein said needle point is exposed to an extended position wherein said needle point is substantially enclosed,
   at least one of said needle means or shield means having a first portion oriented in a nonlinear manner with respect to a second portion thereof, wherein said needle means and said shield means are mountable along the distal end of a syringe; and
   wherein said needle means includes first and second needle sections which are laterally spaced and oriented generally parallel to each other and an angularly oriented third needle section connecting said first and second needle sections, and said shield means is movable generally along said first needle section.

7. A medical device comprising:
   a syringe including a syringe barrel, a plunger movably mounted in said barrel, said syringe having a distal end,
   an elongate and nonlinear needle mounted on said distal end of said syringe and having a skin piercing needle point and distal needle section thereon,
   a hub member adapted to be operatively associated with said needle and mounted adjacent said distal end of said syringe, and
   a protective shield movably mounted adjacent said syringe and adapted to be moved in a linear manner through at least a portion of said hub member between a needle point exposing retracted position and a needle point and distal needle section protecting extended position.

8. A medical device comprising:
   a syringe having an elongate barrel section with a first longitudinal axis, a distal end and a plunger member slidably positioned therein,
   an elongate and nonlinear needle having a skin piercing needle point, said needle adapted to be mountable on said distal end of said syringe,
   a needle shield assembly including a protective shield having at least a portion thereof which has a second longitudinal axis which is laterally offset from said first longitudinal axis,
   a shield support means slidably supporting said protective shield whereby said protective shield is moveable in use between a needle point exposing retracted position wherein said protective shield is laterally offset and substantially separated from said barrel section of said syringe and a needle point protecting extended position wherein said needle point is protected by said protective shield and at least a portion of said needle and needle point are enclosed by said protective shield when said protective shield is in the extended position.

9. A medical device comprising:
   a syringe having an elongate barrel section, a distal end and a plunger member slidably received therein,
   a needle housing operatively associated with the distal end of said syringe assembly,
   an elongate and nonlinear needle means including a portion which is enclosed in said needle housing, said needle means including a skin piercing needle point thereon and first and second needle sections which are laterally spaced apart and generally parallel to each other, and a fluid passageway in said needle housing adapted to provide fluid communication between said first and second needle sections, and
   a protective shield movably mounted in said needle housing and adapted to be slidably movable in said needle housing between an initial start position wherein said needle is partially protected to a retracted position wherein said needle is exposed and to an extended position wherein said needle point and part of said needle means are protected by said protective shield.

10. The medical device of claim 9 wherein said protective shield further includes at least one retaining tab thereon to contact said needle housing and to limit further movement of said protective shield in said needle housing when said protective shield is in the retracted position.

11. The medical device of claim 9 further including a locking tab movably mounted on said protective shield and engaging a locking recess on said needle housing to lock said protective shield in the extended position when said protective shield is moved from the retracted position to the extended position.

12. A medical device comprising:
a needle housing,
an elongate and nonlinear needle means at least a portion of which is enclosed in said needle housing, said needle means including a skin piercing needle point thereon and first and second needle sections which are laterally spaced apart and generally parallel to each other, and a fluid passageway in said needle housing adapted to provide fluid communication between said first and second needle sections,
a protective shield movably mounted in said needle housing and adapted to be slidably movable in said needle housing between an initial start position wherein said needle is partially protected to a retracted position wherein said needle is exposed and to an extended position wherein said needle and needle point are protected, and
further including a start detent movably mounted on said needle housing, said detent engaging a start detent recess in said needle housing to limit movement of said protective shield in said needle housing when said protective shield is in the initial start position.

13. A medical device comprising:
a syringe including a hollow syringe barrel having distal and proximal ends, a plunger movably mounted in said barrel, a mounting means on the distal end of said barrel having a bore therein adapted to be in fluid communication with the interior of said barrel,
an elongate and hollow nonlinear needle including a hub member and distal and proximal hollow needle sections which are laterally offset and generally parallel to each other, and an intermediate hollow needle section which is angularly oriented and fixedly connected between said distal and proximal needle sections, said distal needle section having a skin-piercing needle point on the distal end thereof, and
a protective shield slidably mounted for longitudinal movement through at least a portion of said hub member and said protective shield being movably positioned generally adjacent to said syringe and being slidably movable between a retracted position wherein said needle point is exposed and said protective shield is generally adjacent said syringe barrel and an extended position wherein said distal needle section and said needle point are protected by said protective shield.

14. A medical device particularly adapted to be mounted on a syringe having a hollow syringe barrel and a plunger movably mounted in the syringe barrel and the syringe having a distal end in fluid communication with the interior of the barrel, the medical device comprising:

an elongate and hollow nonlinear needle including distal and proximal needle sections which are laterally spaced apart and generally parallel to each other, and an intermediate means which is angularly oriented and fixedly connected between said distal and proximal needle sections to provide fluid communication therebetween, said distal needle section having a skin piercing needle point on the distal end thereof,
a needle housing particularly adapted to be mounted on the distal end of the syringe and including an angular first passageway therein fixedly enclosing a portion of said needle therein and a second passageway in said needle housing laterally offset from the syringe barrel,
an elongate protective shield slidably mounted in said second passageway, said protective shield including an axially extending slot thereon and a portion of said needle extending therethrough, said protective shield slidably movable between a retracted position wherein said needle point is exposed and an extended position wherein said distal needle section and said needle point are protected by said protective shield, and
a locking means connected between said needle housing and said protective shield to limit the movement of said protective shield in at least one direction of movement with respect to said needle housing.

15. A medical device comprising:
a syringe including a hollow syringe barrel, a plunger movably mounted in said barrel, and a threaded, cylindrical luer-lock collar fixed on the distal end of said barrel, said luer-lock collar having a bore therein in fluid communication with the interior of said barrel,
an elongate and hollow nonlinear needle including distal and proximal hollow needle sections which are laterally offset and generally parallel to each other, and an intermediate hollow needle section which is angularly oriented and fixedly connected between said distal and proximal needle sections, said distal needle section having a skin-piercing needle point on the distal end thereof,
a needle housing including an angular first passageway extending from the proximal end to the distal end of said needle housing, said intermediate needle section of said needle fixed substantially within said first passageway to position said distal needle section laterally offset and distal to said syringe barrel, said needle housing further including a thread engaging needle hub on the proximal end of said needle housing about the proximal end of said first passageway, said needle hub being threadedly connected to said luer-lock collar to fixedly connect said needle housing to said syringe with said needle in fluid communication with the interior of said syringe barrel, said needle housing further including a second passageway laterally offset from said syringe barrel, the distal end of said second passageway receiving portions of said distal and intermediate needle sections of said needle therein, and
an elongate and cylindrical protective shield slidably mounted in said second passageway, said protective shield including an axially extending slot extending from the distal end of said protective shield to a location intermediate of the length of said protective shield, a distal portion of said intermediate needle section extending through said slot, said protective shield slidably movable between a retracted position wherein said distal needle section is exposed to an extended position wherein said distal needle section and said needle point are protected, a first locking means connected betweens said needle housing and said protective shield to prevent the movement of said protective shield in at least one direction of movement with respect to said needle housing when said protective shield is in said retracted position, a second locking means connected between said needle housing and said protective shield to fixedly lock said protective shield in said extended position, and a third locking means connected between said needle housing and said protective shield to prevent the movement of said protective shield in at least one direction of movement with respect to said needle housing when said protective shield is in an intermediate position between said extended and retracted positions.

16. A method for injecting a medication into a patient using a medical device including a syringe having a hollow syringe barrel, a plunger movably mounted in the barrel and a distal end in fluid communication with the interior of the barrel, a needle housing mounted on the distal end of the syringe, the needle housing including first and second passageways therein, the first passageway fixedly retaining a portion of an elongate and hollow nonlinear needle therein and the second passageway including a protective shield slidably mounted therein, the needle including distal and proximal needle sections which are laterally offset and parallel to each other and interconnected by an angularly oriented intermediate needle section to provide fluid communication between the interior of the syringe barrel and a skin-piercing needle point on the distal end of the distal needle section and at least one locking means connected between the needle housing and the protective shield to limit the slidable movement of the protective shield with respect to the needle housing, including the steps of:

placing the medical device in an initial start position wherein the needle in the needle housing is partially enclosed by the protective shield slidably mounted in the needle housing and wherein distal movement of the protective shield along the needle is limited by a contacting relationship between a first locking means connected between the needle housing and the protective shield, moving the protective shield proximally in the needle housing until the needle point on the distal end of the needle is exposed and the protective shield reaches a retracted position, drawing a medication to be injected into a syringe mounted on the needle housing and subsequently injecting the medication into a patient, and sliding the protective shield distally in the needle housing until the protective shield reaches an extended position wherein the protective shield reaches an extended position wherein the protective shield protects the needle and a second locking means connected between the needle housing and the protective shield is locked to prevent proximal movement of the protective shield from the extended position.

17. A medical device comprising:
a syringe assembly having an elongate barrel section, a distal end and a plunger member slidably received therein, a hub member operatively associated with said barrel section, an elongate needle operatively associated with said hub member having a distal needle section and distal needle point thereon, and an elongate protective shield wherein one of said needle or protective shield has an elongate first portion with a first longitudinal axis thereon and an elongate second portion with a second longitudinal axis wherein said first and second longitudinal axes are spaced apart with respect to each other and the other of said needle or protective shield has a third longitudinal axis and wherein said protective shield is operatively associated with said needle and said hub member and movable in use between a retracted position wherein said distal needle section and said distal needle point on said needle are exposed and said barrel section is laterally substantially separated from said protective shield and an extended position wherein said distal needle point and said distal needle section protected by said protective shield in the extended position.

18. The medical device of claim 17 wherein more of said distal needle section is enclosed by said protective shield in the extended position than in the retracted position.

19. The medical device of claim 17 wherein said hub member and said protective shield include a locking means operatively associated therewith to lock said protective shield in the extended position.

* * * * *